United States Patent
Chen et al.

(10) Patent No.: US 11,468,693 B2
(45) Date of Patent: Oct. 11, 2022

(54) DIGITAL IMAGE CLASSIFICATION METHOD FOR CERVICAL FLUID-BASED CELLS BASED ON A DEEP LEARNING DETECTION MODEL

(71) Applicant: Shenzhen Imsight Medical Technology Co., Ltd., Shenzhen (CN)

(72) Inventors: Hao Chen, Shenzhen (CN); Yu Hu, Shenzhen (CN); Zhizhong Chai, Shenzhen (CN); Guangwu Qian, Shenzhen (CN)

( * ) Notice: Subject to any disclaimer, the term of this patent is extended or adjusted under 35 U.S.C. 154(b) by 219 days.

(21) Appl. No.: 17/093,810

(22) Filed: Nov. 10, 2020

(65) Prior Publication Data

US 2022/0083762 A1    Mar. 17, 2022

(30) Foreign Application Priority Data

Sep. 15, 2020 (CN) .......................... 202010967770.9

(51) Int. Cl.
*G06V 20/69* (2022.01)
*G16H 30/20* (2018.01)
(Continued)

(52) U.S. Cl.
CPC ........... *G06V 20/698* (2022.01); *G06N 3/084* (2013.01); *G06T 7/0012* (2013.01);
(Continued)

(58) Field of Classification Search
CPC .... G06V 20/698; G06V 20/695; G16H 30/20; G06N 3/084; G06T 7/0012;
(Continued)

(56) References Cited

U.S. PATENT DOCUMENTS

2018/0068198 A1* 3/2018 Savvides ............ G06V 40/161
2020/0077035 A1* 3/2020 Yao ...................... G06V 20/52

FOREIGN PATENT DOCUMENTS

WO    WO-2021102844 A1 * 6/2021 ........... G06T 7/0012

OTHER PUBLICATIONS

Girshick, Ross. "Fast r-cnn." Proceedings of the IEEE international conference on computer vision. 2015.*
(Continued)

*Primary Examiner* — Shefali D Goradia
(74) *Attorney, Agent, or Firm* — Rumit Ranjit Kanakia

(57) ABSTRACT

The present invention relates to the field of medical technology, and more particularly, to a digital image classification method for cervical fluid-based cells based on a deep learning detection model. The method comprises the following steps: selecting and labeling positions and categories of abnormal cells or biological pathogens in a digital image of cervical liquid-based smears; performing data normalization processing on the digital image of the cervical liquid-based smears; performing model training to obtain a trained Faster-RCNN model by taking the normalized digital image of the cervical liquid-based smears as an input, and the labeled position and category of each abnormal cell or biological pathogen as an output; and inputting an image to be recognized into the trained model and outputting a classification result. The method provided by the embodiment of the present invention can achieve the following advantages: abnormal cells or biological pathogens in a cervical cytological image are positioned; the abnormal cells or biological pathogens in the cervical cytological image are classified; and slice-level diagnostic recommendations are derived by recognizing the positioned abnormal cells or biological pathogens.

10 Claims, 3 Drawing Sheets

(51) Int. Cl.
*G06N 3/08* (2006.01)
*G06T 7/00* (2017.01)

(52) U.S. Cl.
CPC .......... *G06V 20/695* (2022.01); *G16H 30/20* (2018.01); *G06T 2207/20081* (2013.01); *G06T 2207/20084* (2013.01); *G06T 2207/30024* (2013.01)

(58) Field of Classification Search
CPC . G06T 2207/20081; G06T 2207/20084; G06T 2207/30024
See application file for complete search history.

(56) References Cited

OTHER PUBLICATIONS

Redmon, Joseph, et al. "You only look once: Unified, real-time object detection." Proceedings of the IEEE conference on computer vision and pattern recognition. 2016.*

Ren, Shaoqing, et al. "Faster r-cnn: Towards real-time object detection with region proposal networks." Advances in neural information processing systems 28 (2015).*

William, Wasswa, et al. "Cervical cancer classification from Pap-smears using an enhanced fuzzy C-means algorithm." Informatics in Medicine Unlocked 14 (2019): 23-33.*

* cited by examiner

DIGITAL IMAGE CLASSIFICATION METHOD FOR CERVICAL FLUID-BASED CELLS BASED ON A DEEP LEARNING DETECTION MODEL

CROSS-REFERENCE TO RELATED APPLICATIONS

This application claims priority to Chinese Patent Application No. 2020109677709 filed on Sep. 15, 2020, the entire disclosure of which is hereby incorporated by reference for all proper purposes.

TECHNICAL FIELD

The present invention relates to the field of medical technology, and more particularly, to a digital image classification method for cervical fluid-based cells based on a deep learning detection model.

BACKGROUND ART

Cervical cancer is the fourth most common cause of cancer death in women. Early detection and timely treatment of a disease can greatly increase a cure rate. Therefore, the early diagnosis of cervical cancer is of great significance to women's health.

Cervical thin prep liquid-based cytology test (TCT) is a cervical cytological diagnosis method which is often used to detect cervical cancer and other diseases. With the development of medical digitization, modern hospitals are gradually advancing the diagnosis by examining liquid-based cell smear images on a computer, instead of the traditional method of directly observing and diagnosing liquid-based cell smears under a microscope. Digital images have the advantages of easy storage and management, easy transmission and consultation, easy retrospective visits, and relatively low cost of use.

The examination steps for diagnosis on the computer are as follows:

1, a sample of a small amount of cervical cells is first taken to make a cervical liquid-based smear;

2, the cell smear is then scanned with a high-resolution scanner to generate a digital image of the cervical liquid-based smear; and 3, finally, doctors and pathologists observe whether the cells are abnormal and make a diagnosis by using a computer image reading tool.

The cervical liquid-based smear usually contains 5,000-20,000 well-preserved squamous cells or squamous metaplastic cells. In the diagnosis process, the recognition and positioning of abnormal cells or biological pathogens will play a very important role in distinguishing and diagnosing diseased cells and reducing the burden of doctors in screening. Therefore, a cell image automatic positioning and recognition technology will be of great help to computer-aided screening and auxiliary diagnosis.

In view of the recognition and positioning of abnormal cells or biological pathogens in the published patents, the following technical solutions are described.

Patent CN108364032A proposed a cervical cancer cell photo recognition algorithm based on a convolutional neural network. This method comprises the following steps: positioning cell nuclei with a watershed algorithm and segmenting a cell photo with the cell nuclei as centers; then classifying the segmented images by using a LeNet5 convolutional neural network to obtain classification results of the corresponding cells. This patent only involves classifying manually designated cells, but cannot automatically process a digital image of the entire cervical liquid-based smear.

Patent CN109087283A proposes a method for recognizing diseased cells in a cervical cytopathological slice based on cell clusters. This method comprises the following steps: obtaining a foreground image of cell clusters through binarization processing by taking the cell clusters as a processing and recognition unit; and then performing cell cluster classification on the extracted foreground through a classification model of a deep convolutional neural network.

Patent CN109190567A proposed an automatic detection method for abnormal cervical cells based on a deep convolutional neural network. This method is mainly characterized by classifying negative cells (normal cells) in a digital image, while only classifying positive cells into a single category of "positive cervical cells". This patent did not involve a detailed classification of positive cells.

Patent CN110163102A proposed a cervical cell image classification and recognition method based on a convolutional neural network. This method comprises the following steps: segmenting an image into nucleus regions to be detected; and then classifying the segmented nucleus regions by using a dense convolutional network to obtain the categories of cells. This patent did not clearly describe the used image segmentation method, and the used network is a classification network without a positioning function.

The positioning technologies described in the above-mentioned patents have insufficient classification accuracy, and in particular, are difficult to have satisfactory fault tolerance for different slice production methods, such that the sensitivity and specificity of the overall slice-level results are also obviously insufficient.

SUMMARY OF THE INVENTION

In view of the foregoing technical problems, an embodiment of the present invention provides a digital image classification method for cervical fluid-based cells based on a deep learning detection model to solve one or more problems of inaccurate recognition and positioning of abnormal cells or biological pathogens, and low fault tolerance.

In a first aspect of an embodiment of the present invention, there is provided a digital image classification method for cervical fluid-based cells based on a deep learning detection model, which comprises the following steps: a data preparation phase: selecting and marking positions and categories of abnormal cells or biological pathogens in a digital image of cervical liquid-based smears; a data processing phase: performing data normalization processing on the digital image of the cervical liquid-based smears; a model training phase: performing model training to obtain a trained Faster-RCNN model by taking the normalized digital image of the cervical liquid-based smears as an input, and the labeled position and category of each abnormal cell or biological pathogen in the digital image of the cervical liquid-based smears as an output; and an output phase: inputting an image to be recognized into the trained Faster-RCNN model and outputting a classification result.

Optionally, the step of labeling the positions and categories of the abnormal cells or biological pathogens in the digital image of the cervical liquid-based smears specifically comprises: selecting a labeled region in each digital image of the cervical smears; performing rectangular region labeling on abnormal cells or biological pathogens in the labeled region; and recording coordinate positions of upper left and lower right vertices of each rectangle in the rectangle region labeling, and storing the categories of the abnormal cells or the biological pathogens corresponding to the rectangle.

Optionally, a profile of the rectangular region labeling completely covers the region of the abnormal cells or the biological pathogens.

Optionally, the step of performing data normalization processing on the digital image of the cervical liquid-based smears specifically comprises: reading a pixel parameter of each digital image of the cervical liquid-based smears, where the pixel parameter represents an actual distance between each pixel and its corresponding cervical smear; and zooming in and out the digital images of the cervical smears according to the image parameters to realize the normalization of physical dimensions.

Optionally, the pixel parameter is 0.5, and a formula for zooming in and out the digital image of the cervical smears is as follows: the number of pixels in the target line=0.5*the number of pixels in the original line; and the number of pixels in the target column=0.5*the number of pixels in the original column.

Optionally, the method further comprises: performing a flip and/or mirroring operation on the selected digital image of the cervical smears to expand a data set.

Optionally, the output result is predicted probabilities respectively corresponding to the case that the target is a background, abnormal cells or biological pathogens.

Optionally, the model parameters are obtained by training in the model training phase by means of a backpropagation algorithm.

Optionally, the method further comprises: setting a confidence threshold, and displaying a prediction result according to the confidence and calculation rules.

Optionally, the confidence is calculated using the following formula:

$$V=e^{-x^2 \ln 2}$$

wherein, V is the confidence, e is a natural constant, x is a threshold ratio, and ln is a logarithm based on a natural constant.

According to the digital image classification method for cervical fluid-based cells based on the deep learning detection model provided by the embodiment of the present invention, first of all, the fault tolerance of the classification method of the present invention for different slice production methods is improved by using the highly efficient feature extraction capabilities and the diverse training data sets of the deep neural network; secondly, the positioning accuracy is greatly improved by a region proposal network scheme in the target detection model of the deep convolutional neural network; thirdly, the accuracy of the classification of abnormal cells or biological pathogens is effectively improved by a classification network scheme in the target detection model of the deep convolutional neural network; and finally, a whole-slice diagnosis suggestion is obtained with higher sensitivity and specificity by using the rules and formulas designed in the present invention. The digital image classification method for cervical fluid-based cells based on the deep learning detection model provided by the embodiment of the present invention can achieve the following advantages: abnormal cells or biological pathogens in a cervical cytological image are positioned; the abnormal cells or biological pathogens in the cervical cytological image are classified; and slice-level diagnostic recommendations are derived by recognizing the positioned abnormal cells or biological pathogens.

BRIEF DESCRIPTION OF THE DRAWINGS

One or more embodiments are exemplified by the photos in the corresponding accompanying drawings, and these exemplified descriptions do not constitute a limitation on the embodiments. Components with the same reference numerals in the accompanying drawings represent similar components. Unless otherwise stated, the figures in the accompanying drawings do not constitute a limitation of scale.

DETAILED DESCRIPTION

In order to facilitate the understanding of the present invention, the present invention will be further described in detail with reference to accompanying drawings and specific embodiments. It should be also noted that when a component is referred to as "being fixed to" the other component, the component can be directly disposed on the other component, or there may be one or more intermediate components located therebetween. When a component is referred to as "being connected with" the other component, the component can be directly connected to the other component, or there may be one or more intermediate components located therebetween. The orientation or positional relationships indicated by the terms "upper", "lower", "inner", "outer", etc. are orientation or positional relationships shown on the basis of the accompanying drawings, only for the purposes of the ease in describing the present invention and simplification of its descriptions, but not indicating or implying that the specified device or element has to be specifically located, and structured and operated in a specific direction, and therefore, should not be understood as limitations to the present invention. The term "first", "second", "third" and the like used are merely used to describe but not denote or imply any relative importance.

Unless defined otherwise, all technical and scientific terms used herein have the same meaning as commonly understood by those skilled in the art to which the present invention belongs. The terms used herein in the description of the present invention are for the purpose of describing particular embodiments only and are not intended to limit the present invention. The term "and/or" as used herein includes any and all combinations of one or more of the associated listed items.

A deep convolutional neural network has developed rapidly in the field of machine vision in recent years to continuously refresh a number of evaluation records in the academic world, such as the ImageNet Challenge and the MS-COCO Challenge, and thus had a profound impact on the industry. The present invention realizes automatic detection and positioning of various cells in cervical liquid-based cytological images and obtains slice-level diagnosis suggestions on the basis of a target detection model Faster-RCNN of a customized deep convolutional neural network. Meanwhile, according to the following embodiments of the present invention, the model is obtained by deep learning and finite labeled data based on numerical methods, without manually designing features. The data sets constructed by the method of the present invention can also include digital images of different slice production methods and scanning imaging parameters, so that the method of the present invention has stronger versatility and robustness for slice production methods and imaging parameters. The present invention will be described in detail below.

Figure 1:
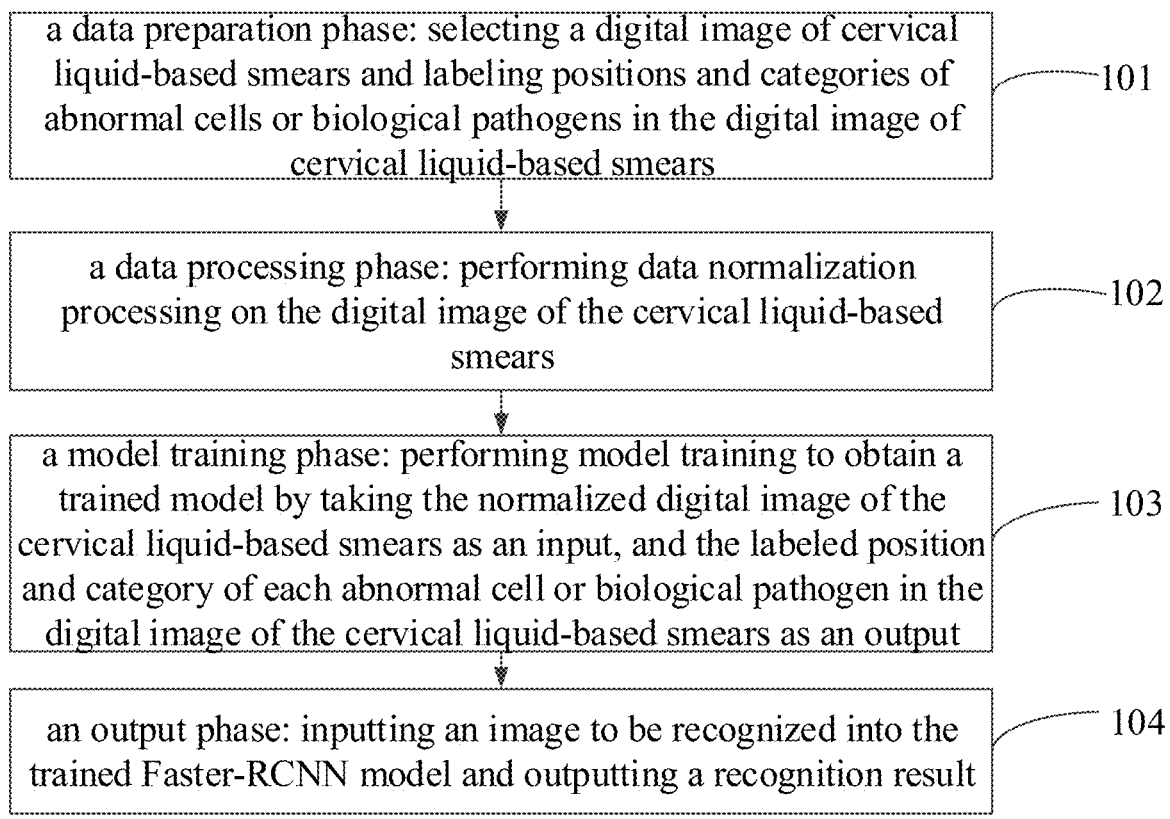
FIG. 1 is a flowchart of a digital image classification method for cervical fluid-based cells based on a deep learning detection model according to an embodiment of the present invention.

Referring to FIG. 1, an embodiment of the present invention first provides a digital image classification method for cervical fluid-based cells based on a deep learning detection model. As shown in FIG. 1, the method comprises the following steps.

Step 101, a data preparation phase: selecting and labeling positions and categories of abnormal cells or biological pathogens in a digital image of cervical liquid-based smears.

Figure 2:
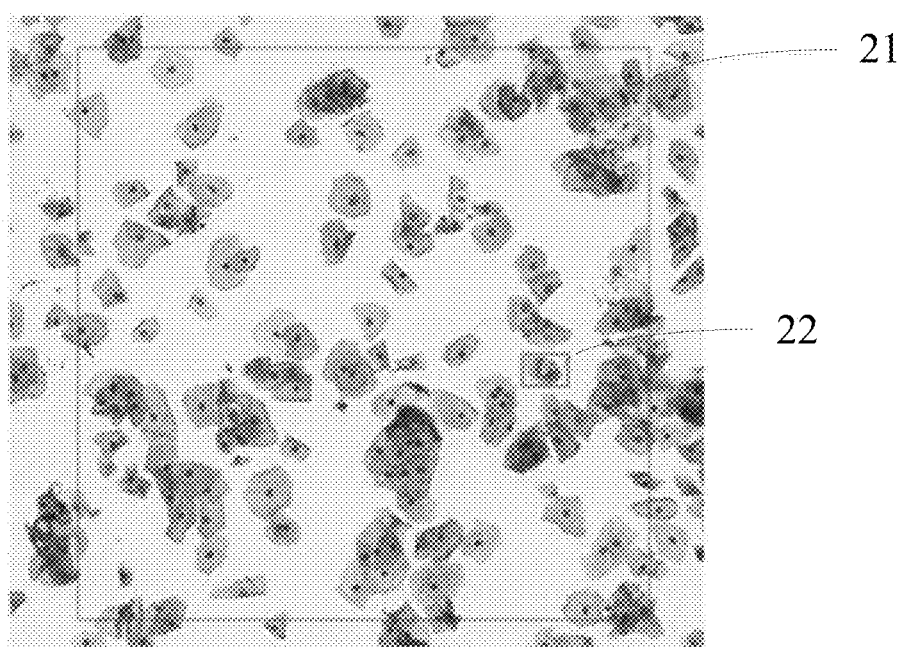
FIG. 2 is a digital image of cervical liquid-based smears that meet clinical standards as provided by an embodiment of the present invention.

According to the method of the present invention, a convolutional neural network for image classification is constructed based on deep learning. Deep learning is a technology in which feature extraction and model parameter adjustment are performed on the basis of a large number of samples through a backpropagation algorithm. In order to solve the problem of positioning and classification of abnormal cells or biological pathogens, in the data preparation phase of the method of the present invention, a digital image containing tens of thousands of cervical liquid-based smears is first constructed, and positions and categories of abnormal cells or biological pathogen nuclei in the digital image of the cervical liquid-based smears are then labelled, which are specifically described as follows:

first of all, digital images of cervical liquid-based smears that meet clinical standards are selected, and a different number of regions containing cells with widths and heights of 1200 pixels are selected from each image at a 20× lens resolution; and the selected regions form labeled regions (21 in FIG. 2). The purpose of selecting the labeled regions in each image is to make a target region fully labeled, while avoiding over-labeling uninteresting regions, thereby saving the manpower and improving the efficiency.

Then, during the labeling process, rectangular labeling and recording of abnormal cells or biological pathogens in the labeled region (22 in FIG. 2) must satisfy: a profile labeled by the rectangle must completely cover the cell or biological pathogen region, while coordinates of the upper left and lower right vertices of each rectangle in the labeled region need to be completely recorded, and the categories of the abnormal cells or biological pathogens corresponding to the rectangle are stored.

In an embodiment of the present invention, the categories of abnormal cells or biological pathogens that need to be labeled are as follows:

squamous cells include: atypical squamous epithelial cells (low-grade squamous epithelial lesions, not excluding high-grade squamous epithelial lesions) and squamous cell carcinoma (high-grade squamous epithelial lesions);

glandular cells include: atypical glandular cells (cervical canal cells, endometrial cells), cervical canal glandular cells (prone to be tumorous), cervical canal adenocarcinoma in situ, adenocarcinoma (cervical canal adenocarcinoma, endometrial adenocarcinoma, extrauterine adenocarcinoma);

biological pathogens include: *Trichomonas vaginalis*, fungi with morphology consistent with *Candida albicans* (bacterial vaginosis is suggested in the case of dysbacteriosis), and bacteria with morphology consistent with actinomycetes (cytological changes accord with herpes simplex virus infection);

and endometrial cells.

Step 102, a data processing phase: performing data normalization processing on the digital images of the cervical liquid-based smears.

The images selected in step 101 are all sampled from different digital images of cervical liquid-based smears, and these digital images may be scanned and imaged by different scanners. Therefore, the collected images needs to be normalized, due to the difference in hardware attributes and software parameter settings of different scanners, and the difference in actual physical dimensions represented by pixels of each image. The purpose of normalization is to ensure that the images in a data set have similar physical dimensions as much as possible. In the deployment and application scenarios of the following deep convolutional neural network model, input data should also be normalized in the same way.

According to an embodiment of the present invention, a micron per pixel (mpp) parameter of an image can be obtained by reading additional information of the image. As a pixel parameter, mpp represents an actual distance of a cervical smear corresponding to each pixel, and mpp of 1 represents that an actual horizontal or longitudinal distance represented by each pixel is 1 micron.

By reading the mpp, the images in the digital image data set of the cervical smears can be zoomed in or out by bilinear interpolation to achieve the normalization of physical dimensions of the data.

In the method of the present invention, the data set mpp is normalized to 0.5. The number of pixels in a target line (column) of each photo is calculated by the following formula:

the number of pixels in the target line (column)=0.5*the number of pixels in the original line (column)/mpp.

Step 103, a model training phase: performing model training to obtain a trained model by taking the normalized digital image of the cervical liquid-based smears as an input, and the labeled position and category of each abnormal cell or biological pathogen in the digital image of the cervical liquid-based smears as an output.

In this step, the Faster-RCNN deep convolutional neural network model is trained to obtain the trained network model by taking the corresponding coordinates and category corresponding to rectangular region labeling of each abnormal cell or the biological pathogen in the image as the output.

In the embodiment of the present invention, in order to use the finite training data to make the generalization ability of the model stronger, the digital images of the cervical smears in the training set can be flipped and/or mirrored to realize the expansion of the data set. For ease of description, a data set composed of originally selected digital images of cervical smears is named a training set (1) below. Taking the training set (1) as basic data, the specific steps for data set expansion are as follows:

mirroring: the training data set (1) and labeled images thereof are mirrored vertically or horizontally at the same time, and are then aggregated with the training data set (1) to form a training data set (2).

flip: the training data set (2) and labeled images thereof are flipped clockwise at the same time, at a flip angle of 90 degrees, 180 degrees or 270 degrees, and are then aggregated with the training data set (2) to form a training data set (3). The expanded training data set (3) includes training data used to train a neural network.

Figure 3:
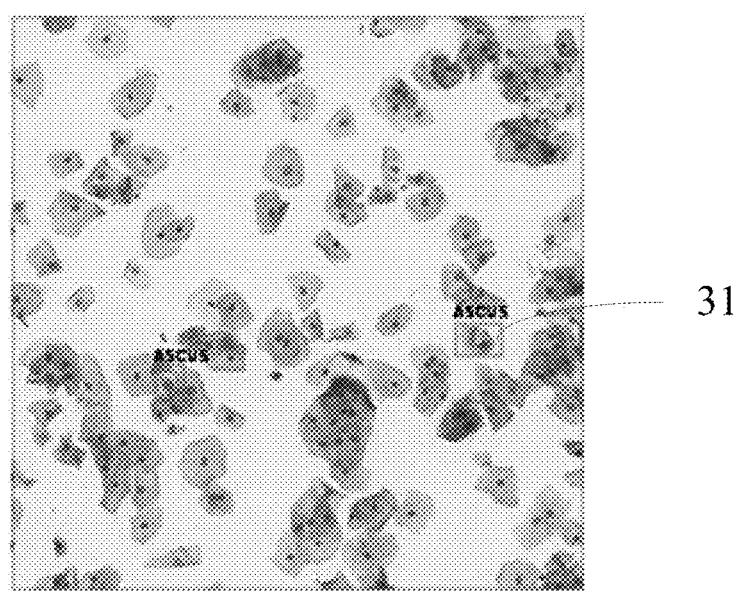
FIG. 3 is a digital image of cervical liquid-based smears in a labeled region as provided by an embodiment of the present invention.

The expanded training data set (3) is input into the Faster-RCNN deep convolutional neural network model of the present invention for training. When the deep convolutional neural network model is trained, a digital image of cervical liquid-based smears of 1200×1200 pixels is taken as an input of the model, and coordinates and a category label (31 in FIG. 3) of a label box of each abnormal cell or biological pathogen in the image is taken as an output of the model. It should be noted that the above-mentioned mirroring followed by flipping is only one of the embodiments of the present invention to expand the training set. In other embodiments, the training set may also be expanded by flipping followed by mirroring, or only by flipping, or only by mirroring.

The training model used in the method of the present invention is the Faster-RCNN model. The Faster-RCNN model is an image segmentation model based on a convolutional neural network. It is unnecessary to manually design features for this model. A large amount of labeled data can be used to train the model to obtain a good positioning and classification effect. In the embodiment of the present invention, training the model includes the following steps.

1. Feature Extraction Network

In the training process, a digital image of cervical liquid-based smears of 1200*1200 pixels is input into the deep convolutional neural network for feature extraction. The feature extraction network consists of repeatedly stacked convolutional layers, sampling layers and nonlinear activation layers. This neural network architecture summarizes and extracts abstract features of an image by pre-training with a large amount of image data and category labels of objects contained in the images on the basis of the back-propagation algorithm in deep learning, and outputs a high-dimensional feature tensor of the image.

The feature extraction network applied in the embodiment of the present invention is a feature extraction network of a modified Resnet-101 classification network. A network architecture diagram of the feature extraction network is shown in Table 1, where there is no non-linear activation layer between respective cycles. A 1200*1200 image is taken as an input of the feature extraction network, and four high-dimensional tensors of 300*300*2048, 150*150*2048, 75*75*2048, 38*38*2048 are taken as an output of the feature extraction network.

TABLE 1

| Name of layer | Input dimension | Size of computing core | Step length | Module cycle |
|---|---|---|---|---|
| Input | 1200*1200*3 | — | — | |
| Convolution 1 | 600*600*64 | 7*7 | 2 | |
| Layer 1.0. Pooling | 300*300*256 | 1*1 | 2 | |
| Layer 1.0. Convolution 1 | 300*300*64 | 1*1 | 1 | 3 cycles |
| Layer 1.0. Convolution 2 | 300*300*64 | 3*3 | 1 | |
| Layer 1.0. Convolution 3 | 300*300*256 | 1*1 | 1 | |
| Layer 2.0. Pooling | 150*150*512 | 1*1 | 2 | |
| Layer 2.0. Convolution 1 | 150*150*128 | 1*1 | 1 | 4 cycles |
| Layer 2.0. Convolution 2 | 150*150*128 | 3*3 | 1 | |
| Layer 2.0. Convolution 3 | 150*150*512 | 1*1 | 1 | |
| Layer 3.0. Pooling | 75*75*1024 | 1*1 | 2 | |
| Layer 3.0. Convolution 1 | 75*75*256 | 1*1 | 1 | 23 cycles |
| Layer 3.0. Convolution 2 | 75*75*256 | 3*3 | 1 | |
| Layer 3.0. Convolution 3 | 75*75*1024 | 1*1 | 1 | |
| Layer 4.0. Pooling | 38*38*2048 | 1*1 | 2 | |
| Layer 4.0. Convolution 1 | 38*38*512 | 1*1 | 1 | 3 cycles |
| Layer 4.0. Convolution 2 | 38*38*512 | 3*3 | 1 | |
| Layer 4.0. Convolution 3 | 38*38*2048 | 1*1 | 1 | |

2. Region Propose Network

Then, the extracted deep convolution features are input into a region proposal network. The region proposal network is composed of fully connected layers and nonlinear activation layers. The region proposal network performs sliding window classification and object bounding box coordinate regression on the high-dimensional tensors output by the feature extraction network. The classification result refers to determining a probability that the current window position contains abnormal cells or biological pathogens and estimating dimensions and aspect ratios of the cells contained in the current window. The current window position corresponds to the corresponding coordinate position in the original image.

A network architecture diagram of the region proposal network is shown in Table 2. According to the embodiment of the present invention, a 3*3*256 convolution and a sliding window along the first two dimensions on the corresponding four high-dimensional tensors are taken as an input of the region proposal network. An intermediate layer is a 256-dimensional feature vector. A classification output layer is the fully-connected layer. The fully-connected output of the 256-dimensional feature vector is the categories of objects included in the current region, wherein the vector [0,1] represents a background, the vector [1,0] represents abnormal cells or biological pathogens, and the rectangular box position regression also occurs in the fully-connected layer. The fully-connected output of the 256-dimensional vector is floating point values of the objects included in the current region in [0,1] relative to the normalization of the lengths and the widths in horizontal and longitudinal directions of coordinates of the upper left corner of an external rectangular box in the center of sub-tensor coordinates.

TABLE 2

| Name of layer | Input dimension | Size of computing core | Step length | Description |
|---|---|---|---|---|
| fpn. inner layer 1 | 300*300*256 | 1*1 | 1 | Pooling |
| fpn. layer 1 | 300*300*256 | 3*3 | 1 | Convolution |
| fpn. inner layer 2 | 150*150*256 | 1*1 | 1 | Pooling |
| fpn. layer 2 | 150*150*256 | 3*3 | 1 | Convolution |
| fpn. inner layer 3 | 75*75*256 | 1*1 | 1 | Pooling |
| fpn. layer 3 | 75*75*256 | 3*3 | 1 | Convolution |
| fpn. inner layer 4 | 38*38*256 | 1*1 | 1 | Pooling |
| fpn. layer 4 | 38*38*256 | 3*3 | 1 | Convolution |
| rpn. Pooling | 7*7*256 | 3*3 | 1 | Pooling |

TABLE 2-continued

| Name of layer | Input dimension | Size of computing core | Step length | Description |
|---|---|---|---|---|
| rpn. Classification | 2*12544 | 1*1 | 1 | Fully-connected layer |
| rpn. Border prediction | 8*12544 | 1*1 | 1 | Fully-connected layer |

3. Classification Network

At last, the classification network classifies the high-dimensional feature tensors corresponding to positions containing abnormal cells or biological pathogens output by the region proposal network, and determines that a target contained in this region is abnormal cells, or detailed categories of biological pathogens or a background. The classification network is composed of stacked fully-connected layers and nonlinear activation layers. A network architecture diagram of the classification network is shown in Table 3. The image scale of the feature extraction network is reduced by 32 times from input to output. Therefore, the lengths and widths in the horizontal and longitudinal directions output by the region proposal network need to be enlarged by 32 times, which is the size of a detection box in the original image.

TABLE 3

| Name of layer | Input dimension | Size of computing core | Step length | Description |
|---|---|---|---|---|
| roi. fully-connected layer 6 | 1024 | — | — | |
| roi. fully-connected layer 7 | 1024 | — | — | |
| roi. classification output | 16 | — | — | 16 represents 16 categories of classification results |

In the above-mentioned neural network architecture of the present application, the nonlinear activation layer adopts a rectified linear unit (ReLU), and the convolutional layer and the fully-connected layer are followed by the nonlinear activation layer of the ReLU function. The formula of ReLU is as follows, wherein max represents a maximum taken from two input numbers:

$$ReLU(x)=\max(0, x)$$

According to the embodiment of the present invention, the backpropagation algorithm in deep learning is used for training to obtain model parameters. The classification network and the region proposal network take a target real category vector and the coordinates of the input region relative to the coordinates of the center of the input tensor as labels, and the loss function is a cross entropy function.

In the embodiment of the present invention, the parameters of the feature extraction network are initialized by removing the parameters of the fully-connected layer from a network pre-trained in the ImageNet classification network. Other relevant network parameters are randomly initially selected from parameters in [0,1] that obey the truncated normal distribution. A stochastic gradient descent backpropagation algorithm is used to train 90 cycles in an enhanced training set with a learning rate of 0.001.

After the above training is completed, segmentation results are counted through the obtained model on a verification set. That is, all the segmentation results of each image in the verification set are superimposed together to form a segmentation template of this image. Finally, a Euclidean distance between the segmentation template and the actual label is calculated. The Euclidean distance is an inference error of a single image. At last, the inference errors of all the images in the verification set are added to obtain a verification set error. In the training process selected in the embodiment of the present invention, a model with the minimum verification set error is selected as the Faster-RCNN model obtained by final training.

In the embodiment of the present invention, a region with a maximum predicted probability higher than a threshold of 0.4 is regarded as the final output of the model. All targets output by the model are processed with a non-maximum suppression (NMS) algorithm to eliminate highly overlapping detection results and regarded as the final output of the algorithm. In the present invention, redundant calculations in image operations can be reduced by adaptive thresholds and the NMS algorithm, thereby achieving a huge improvement in image processing efficiency.

Step 104, an output phase: inputting an image to be recognized into the trained Faster-RCNN deep convolutional neural network model and outputting a classification result.

In application, the output of the classification network is a predicted probability that this target region is a background, abnormal cells or biological pathogens. In this step, a digital image of cervical liquid-based cells to be recognized needs to be input into the trained Faster-RCNN deep convolutional neural network model. By means of the above-mentioned feature extraction, the selection of the region proposal network and final classification, different numbers of abnormal cells or biological pathogens and their corresponding predicted probabilities are obtained.

According to the digital image classification method for cervical fluid-based cells based on the deep learning detection model provided by the embodiment of the present invention, any digital image of cervical liquid-based smears is inputted into the Faster-RCNN model obtained in Step 103 to obtain whether the target is abnormal cells, the detailed categories of biological pathogens, or the background. It should be noted that the model training method in the embodiment of the present invention is as a result of the creative work of those skilled in the art. Any change, adjustment, or replacement scheme for the data enhancement method, neural network architectures, hyperparameters, and loss function in the present invention on the basis of the embodiments of the present invention should be regarded as being equivalent to this solution.

After the predicted probability that the target is abnormal cells, the detailed categories of biological pathogens, or the background is obtained, the user can set a confidence threshold to display a predicted result that is greater than the set confidence threshold.

In the present invention, a confidence calculation method is as follows:

first of all, for each category without background, 16 detection results with the maximum probabilities are selected as basic data for the calculation of smear results in the embodiment of the present invention (all detection results are used as the basic data for the calculation of the smear results if there are less than 16 detection results).

For each category, the selected basic data are averaged to obtain a score of this category, and a score-to-threshold ratio of this category is obtained by dividing the score by the corresponding threshold. Through the score-to-threshold ratio, the confidence of slice-level results is then obtained by the following formula:

$$V=e^{-x^2 \ln 2}$$

where V is the confidence, e is a natural constant, x is a score-to-threshold ratio, and ln is a logarithm based on a natural constant.

After the confidence of each category is obtained, in the embodiment of the present invention, the confidence of the category is considered as a potential category if it exceeds 0.5.

In the embodiment of the present invention, the potential category of abnormal cells will obtain a final slice-level result according to the following priority. If there is no potential category, the result is negative:

atypical glandular cells (including cervical canal and endometrial cells)>high-grade squamous epithelial lesions>atypical squamous epithelial cells (not excluding high-grade squamous epithelial lesions)>low-grade squamous epithelial lesions>atypical squamous epithelial cells (undefined).

The potential categories of biological pathogens will all be listed as results. If there are no potential categories, the result will be negative.

After the confidence of each category of cells is obtained, it is necessary to further rank the confidence of each category of abnormal cells in a descending order. The positive confidence in each smear can be obtained by continuously applying the following formulas in pairs successively:

$$\amalg(V_1, V_2) \begin{cases} \frac{V_1 + V_2}{1 + 4V_1 V_2}; & \text{if } V_1, V_2 < 0.5 \\ \frac{V_1 + (V_2 - 0.5)}{1 + V_1(V_2 - 0.5)}; & \text{if } V_1, V_2 > 0.5 \\ V_1; & \text{other cases} \end{cases}$$

in which, V1 and V2 are two confidences entered in the applying process. For example, for the existing confidences V1, V2, V3, and V4 ranked in a descending order, the formula will be applied three times in succession when calculating the confidence, as shown in the following formula:

$$\text{Confidence} = \amalg(\amalg(\amalg(V_1, V_2), V_3), V_4)$$

In the embodiment of the present invention, first of all, the fault tolerance of the classification method of the present invention for different slice production methods is improved by using the highly efficient feature extraction capabilities and the diverse training data sets of the deep neural network; secondly, the positioning accuracy is greatly improved by the region proposal network (RPN) scheme in the target detection model of the deep convolutional neural network; thirdly, the accuracy of the classification of abnormal cells or biological pathogens is effectively improved by a classification network scheme in the target detection model of the deep convolutional neural network; and finally, a whole-slice diagnosis suggestion is obtained with higher sensitivity and specificity by using the rules and formulas designed in the present invention. That is, the digital image classification method for cervical fluid-based cells based on the deep learning detection model provided by the embodiment of the present invention can achieve the following advantages:

1. abnormal cells or biological pathogens in a cervical cytological image are positioned;

2. the abnormal cells or biological pathogens in the cervical cytological image are classified; and 3. slice-level diagnostic recommendations are derived by recognizing the positioned abnormal cells or biological pathogens.

Compared with Patent CN108364032A, the method of the present invention can not only automatically position abnormal cells that need to be classified, but also position and recognize biological pathogens.

Compared with Patent CN109087283A, the method of the present invention can not only recognize abnormal cells and biological pathogens in cell clusters, but also can recognize and position discrete cells with high accuracy. In addition, the pre-processing process is more concise and faster.

Compared with the patent CN109190567A, the method of the present invention can effectively classify positive abnormal cells and biological pathogens in detail.

Compared with the patent CN110163102A, the method of the present invention adopts automatic effective region segmentation, and automatic positioning of abnormal cells and pathogenic microorganisms, thereby saving a lot of manpower.

Therefore, compared with the above four patents, the method of the present invention can not only realize the positioning and classification of abnormal cells or biological pathogens on the digital images of the cervical liquid-based smears, but also can give diagnosis suggestions on the slice-level results, which play an auxiliary role for clinicians, thereby reducing the workload of doctors. At the same time, the slice-level diagnosis suggestions given by the present invention have higher sensitivity and specificity. It should be noted that the method of the present invention can also be applied to automatic detection of other pathological digital images in the medical field, such as the detection of exfoliated cells of urine, which will not be limited in the present invention.

It should be further appreciated by those skilled in the art that, various steps of the exemplary bifocal image integration method described in conjunction with the embodiments disclosed herein may be implemented as electronic hardware, computer software or a combination thereof. In order to clearly illustrate the interchangeability between the hardware and the software, the constitution and steps of various examples are described generally according to the functions in the above description. Whether these functions are implemented as hardware or software depends on particular applications and design constraints of technical solutions.

Those skilled in the art may implement the described functions with different methods for each of particular applications, but such implementation shall not be regarded as going beyond the scope of the present invention. The computer software may be stored in a computer readable storage medium, and when this program is executed, the processes of the above-mentioned method embodiments will be included. The storage medium may be a magnetic disk, an optical disc, a read-only storage memory, a random storage memory, or the like.

It should be eventually noted that: the above embodiments are only used to illustrate the technical solutions of the present invention, rather than limiting these technical solutions; under the concept of the present invention, the technical features in the above embodiments or different embodiments can also be combined, the steps can be implemented in any order, and there are many other variations of different aspects of the present invention as described above, which are not provided in the details for the sake of clarity. Although the present invention has been described in detail with reference to the foregoing embodiments, those of ordinary skill in the art should understand: it is still possible to modify the technical solutions described in the foregoing embodiments, or equivalently replace some of the technical features. However, these modifications or replacements do not cause the essence of the corresponding technical solutions to deviate from the scope of the technical solutions of the embodiments of the present invention.

What is claimed is:

1. A digital image classification method for cervical fluid-based cells based on a deep learning detection model, comprising the following steps:
    a data preparation phase: selecting and labeling positions and categories of abnormal cells or biological pathogens in a digital image of cervical liquid-based smears;
    a data processing phase: performing data normalization processing on the digital image of the cervical liquid-based smears;
    a model training phase: performing model training to obtain a trained Faster-RCNN model by taking the normalized digital image of the cervical liquid-based smears as an input, and the labeled position and category of each abnormal cell or biological pathogen in the digital image of the cervical liquid-based smears as an output; and
    an output phase: inputting an image to be recognized into the trained Faster-RCNN model and outputting a classification result.

2. The method as claimed in claim 1, wherein the step of labeling the positions and categories of the abnormal cells or biological pathogens in the digital image of the cervical liquid-based smears specifically comprises:
    selecting a labeled region in each digital image of the cervical smears;
    performing rectangular region labeling on the abnormal cells or biological pathogens in the labeled region; and
    recording coordinate positions of upper left and lower right vertices of each rectangle in the rectangle region labeling, and storing the categories of the abnormal cells or the biological pathogens corresponding to the rectangle.

3. The method as claimed in claim 2, wherein a profile of the rectangular region labeling completely covers the region of the abnormal cells or the biological pathogens.

4. The method as claimed in claim 2, wherein the output result is predicted probabilities respectively corresponding to the case that the target is a background, abnormal cells or biological pathogens.

5. The method as claimed in claim 1, wherein the step of performing data normalization processing on the digital image of the cervical liquid-based smears specifically comprises:
    reading a pixel parameter of each digital image of the cervical liquid-based smears, where the pixel parameter represents an actual distance between each pixel and its corresponding cervical smear; and
    zooming in and out the digital images of the cervical smears according to the image parameters to realize the normalization of physical dimensions.

6. The method as claimed in claim 5, wherein the pixel parameter is 0.5, and a formula for zooming in and out the digital images of the cervical smears is as follows:
    the number of pixels in the target line=0.5*the number of pixels in the original line; and
    the number of pixels in the target column=0.5*the number of pixels in the original column.

7. The method according to claim 1, further comprising: performing a flip and/or mirroring operation on the selected digital images of the cervical smears to expand a data set.

8. The method as claimed in claim 1, wherein model parameters are obtained by training in the model training phase by means of a backpropagation algorithm.

9. The method as claimed in claim 1, further comprising: setting a confidence threshold, and displaying a prediction result according to the confidence and calculation rules.

10. The method as claimed in claim 9, wherein the confidence is calculated using the following formula:

$$V=e^{-x^2 \ln 2}$$

wherein, V is the confidence, e is a natural constant, x is a score-to-threshold ratio, and ln is a logarithm based on a natural constant.

* * * * *